(12) United States Patent
Bentsen et al.

(10) Patent No.: US 7,220,344 B2
(45) Date of Patent: *May 22, 2007

(54) FILM BASED ADDRESSABLE PROGRAMMABLE ELECTRONIC MATRIX ARTICLES AND METHODS OF MANUFACTURING AND USING THE SAME

(75) Inventors: James Gregory Bentsen, North Saint Paul, MN (US); Rolf Werner Biernath, Maplewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 150 days.

This patent is subject to a terminal disclaimer.

(21) Appl. No.: 10/200,829

(22) Filed: Jul. 23, 2002

(65) Prior Publication Data

US 2002/0195345 A1 Dec. 26, 2002

Related U.S. Application Data

(62) Division of application No. 09/447,471, filed on Nov. 18, 1999, now Pat. No. 6,451,191.

(51) Int. Cl.
*G01N 27/447* (2006.01)
*G01N 27/453* (2006.01)

(52) U.S. Cl. ..................... 204/450; 204/600
(58) Field of Classification Search ............... 204/600, 204/606, 616, 450, 456, 466
See application file for complete search history.

(56) References Cited

U.S. PATENT DOCUMENTS

| 5,344,701 | A | 9/1994 | Gagnon et al. |
|---|---|---|---|
| 5,401,913 | A | 3/1995 | Gerber et al. |
| 5,417,835 | A | 5/1995 | Brown et al. |
| 5,605,662 | A | 2/1997 | Heller et al. |
| 5,609,828 | A | 3/1997 | O'Bear et al. |
| 5,632,957 | A | 5/1997 | Heller et al. |
| 5,653,939 | A | 8/1997 | Hollis et al. |
| 5,725,989 | A | 3/1998 | Chang et al. |
| 5,929,208 | A | 7/1999 | Heller et al. |
| 5,965,452 | A | 10/1999 | Kovacs |
| 6,039,897 | A | 3/2000 | Lochhead et al. |
| 6,151,519 | A | 11/2000 | Sugihara et al. |
| 6,225,059 | B1 | 5/2001 | Ackley et al. |
| 6,238,624 | B1 | 5/2001 | Heller et al. |
| 6,287,517 | B1 | 9/2001 | Ackley et al. |
| 6,451,191 | B1 * | 9/2002 | Bentsen et al. ............. 204/600 |

FOREIGN PATENT DOCUMENTS

| WO | WO 94 16803 A | 8/1994 |
|---|---|---|
| WO | WO 96 42013 A | 12/1996 |
| WO | WO 99 15888 A | 4/1999 |
| WO | WO 99 19717 A | 4/1999 |
| WO | WO 99 45375 A | 9/1999 |

\* cited by examiner

*Primary Examiner*—Alex Noguerola
(74) *Attorney, Agent, or Firm*—Philip Y. Dahl; John M. Bronk

(57) ABSTRACT

An electronic device adapted for performing molecular biological processes. The device includes a flexible polymeric substrate having a first surface and a second surface. A plurality of microlocations interrupt the first surface, and each of said microlocations include an electrode disposed on the second surface of the flexible substrate. A hydrophilic matrix is positioned on the first surface of the flexible substrate and is capable of electrical contact with the electrode.

28 Claims, 7 Drawing Sheets

FILM BASED ADDRESSABLE PROGRAMMABLE ELECTRONIC MATRIX ARTICLES AND METHODS OF MANUFACTURING AND USING THE SAME

CROSS REFERENCE TO RELATED APPLICATIONS

This application is a divisional of U.S. application Ser. No 09/447,471, filed Nov. 18, 1999, now allowed as U.S. Pat. No. 6,451,191, the disclosure of which is herein incorporated by reference.

FIELD OF THE INVENTION

This invention relates to film based addressable programmable electronic matrix articles and methods for manufacture and use of the same. The articles are manufactured on a flexible film, and are suited for use with patterned polymer films tailored to selectively bind or react with various target species, including biologically active molecules.

BACKGROUND OF THE INVENTION

One of the most important activities of modern medical and biochemical fields is conducting medical diagnostic assays, such as cell culture assays, immunoassays, DNA hybridization assays, robot assisted sample handling processes, and microfluid sample processing. These activities permit safe and effective medical diagnoses, as well as thorough and accurate biochemical investigations and research.

Automated microbial culturing systems have been developed in recent years to test for a variety of diseases in a clinical laboratory setting. These systems often include culture tubes containing samples, selective growth media, and a fluorescent indicator that responds to the growth of the microorganisms. The tubes are continually processed by an optical reader that measures changes in fluorescent properties of the sample in order to detect such microbes as tuberculosis or antibiotic resistant *Staph. aureus*. Unfortunately, such systems can take days to culture a sufficient quantity of the microbes necessary for identification with standard test methods.

Biocards, such as those described in U.S. Pat. No. 5,609,828, have also been developed to carry out multiple assays from a single sample extracted from blood, fluids, or other tissue of a patient. These samples are usually examined using spectroscopic or other automated analysis techniques. Biocards are typically molded in plastic and are designed to receive a liquid sample into a series of small sample wells formed in the card. Each sample well normally contains a different set of dried reagent (selective growth nutrients and indicator dies) for identifying different biological agents within the sample. During analysis, the sample enters an intake port, collects in an intake reservoir, and travels along distribution channels to the sample wells. Each sample well also typically includes a bubble trap designed to trap gases formed by growing microorganism colonies. The reagents within the sample wells dissolve when the fluid sample is introduced. After incubation of the sample in the sample wells, a card reader performs automated spectroscopic or fluorescence analysis on each well. Although analysis with biocards can be successful, analysis times are quite long unless the microorganisms are first cultured to increase their number. In addition, closely related strains of microorganisms are hard to differentiate by these methods.

Efforts have been made to develop assay techniques for the analysis of nucleic acids and proteins that shorten the delay associated with culture techniques, increase the specificity of the assays, and provide means for detecting new diseases. One such effort has been the development of DNA amplification technologies that provide a means to produce hundreds of millions of copies of a selected DNA target in less than one hour. Microorganisms of interest are first lysed to release their DNA material. The DNA material is isolated and then treated with reagents to perform an amplification of an oligonucleotide sequence specific to the microorganism of interest. While polymerase chain reaction (PCR) is the most well known of these amplification methods, it requires temperature cycling and continued reagent additions. Other methods, such as a strand displacement amplification approach developed at Becton Dickinson of Franklin Lakes, N.J., can be performed in a single sample well in 15 minutes at constant temperature. Such amplification methods help to overcome problems related to complexity and sensitivity in genomic DNA analysis.

Once the DNA target has been "amplified" by reproduction to produce numerous amplicons, complementary oligonucleotide probes can be used to capture the DNA amplicons. These probes selectively retain the DNA amplicon, allowing them to be isolated and identified. However, these probes have traditionally relied upon diffusion controlled processes to capture the DNA amplicons. Diffusion can take hours to complete, and is a significant hurdle to rapid identification of the DNA target. Although such diffusion methods are significantly quicker than prior cell culture techniques, they are still relatively slow compared to the rapid rate of DNA amplification.

An alternative to DNA amplification, known as the Southern Blot, involves cleaving the DNA with restrictive enzymes, separating the DNA fragments on an electrophoresis gel, blotting to a membrane filter, and then hybridizing the blot with specific DNA probe sequences. This procedure effectively reduces the complexity of the crude DNA sample, thereby helping to improve the hybridization specificity and sensitivity. However, the total number of targets generated in a Southern Blot is far less than the number of amplicons generated by DNA amplification methods. In addition, the electrophoretic separation can take hours to complete.

Recently, efforts have been made to hasten the separation and capture of DNA amplicons. Researchers have developed micro-electrode arrays that speed up the capture process by using free-field electrophoresis to concentrate and purify target DNA on the individual probes of the array. These arrays create a charged electrical field that isolates the charged DNA amplicons at one or more probes on the array. This type of microelectronic array, known as an "addressable programmable electronic matrix" ("APEX"), can reduce the time to perform the capture process from hours to minutes. A number of patents describe silicon based chips having APEX arrays. For example, U.S. Pat. Nos. 5,653,939 and 5,632,957 teach the manufacture of rigid silicon APEX arrays using a lithographic process. Although these silicon APEX arrays permit enhanced capture rates, they are relatively expensive to produce. Also, they cannot be easily reused without being cleaned and repatterned with DNA probes in a manufacturing environment. Even though they are relatively expensive, the silicon APEX arrays are typically used once and then discarded.

Thus, existing APEX arrays have improved the speed of performing DNA identification tests, but have failed to address the need for cost-effective, mass manufacturable APEX assay systems. In view of the significant expense associated with existing APEX chip systems, a need exists for an APEX chip that provides the increased speed of a programmable microelectronic matrix, but can be done for less expense than existing silicon-based chips.

SUMMARY OF THE INVENTION

The present invention is directed to a film based microelectrode array device adapted for processing of chemical, biological, or particulate materials at electronically addressed micro-locations. Uses for the device include chemical- and molecular biological-type analyses, including nucleic acid hybridization reactions, antibody/antigen reactions, various cell sorting operations, and synthesis reactions including DNA amplifications and various free-field electrophoresis manipulations.

In specific implementations, the device includes a flexible polymeric substrate having a first or upper surface and a second or lower surface. A plurality of microlocations interrupts the first surface, and each of these microlocations preferably includes an electrode disposed on the first or second surface of the flexible substrate. Circuit traces connect the electrodes to larger contact pads also disposed on the first or second surface of the flexible substrate. A hydrophilic permeation matrix and optionally a biologically receptive polymer is positioned on the first surface of the flexible substrate and is capable of supporting electrical contact between the electrode and a fluid sample placed in contact with the first surface of the flexible substrate. Flexible polymeric substrates of the present invention are particularly well suited for the manufacture of APEX chips and enable the manufacture of novel APEX biocards, and APEX spools.

In certain implementations of the invention, the flexible polymeric substrate is formed of polyimide. The flexible polymeric substrate may be completely, substantially, or partially formed of the polyimide, and may be combined with other materials. It will be appreciated that the invention is also directed to any flexible substrate that permits the formation of a first surface and a second surface, with electrodes interrupting the first surface. The substrate and electrodes should also permit the retention of a hydrophilic permeation matrix, such as a derivitizable gel, in a manner such that programmable free-field electrophoresis processes can be conducted using the substrate and electrodes. The hydrophilic permeation matrix may include a biologically receptive gel, or may have inherent biological receptive properties.

In one implementation, the plurality of microlocations interrupting the first surface includes vias that extend from the first surface into the polymeric substrate. The vias provide a location for the formation of the electrodes. The electrodes are formed, for example, by securing a conducting metallic layer on the second or lower surface of the flexible substrate and then selectively removing the polymeric substrate above the conducting metallic layer. The polymeric substrate is selectively removed to expose the conducting metallic layer, thereby forming electrodes. Removal of the substrate is performed by chemical etching methods, plasma removal methods, laser removal methods, or other suitable methods.

In other examples, the electrodes are formed by depositing a metallic layer on the first or upper surface of the flexible polymeric sheet. After the metallic layer is deposited, a non-conductive masking layer is applied over the metallic layer. This masking layer is selectively removed by an appropriate methodology, such as photo-lithography, in order to expose portions of the metallic layer to form a plurality of exposed electrodes.

It will also be appreciated that in certain implementations of the invention the electrodes formed by exposure of the metal layer may subsequently be enlarged by deposition of additional metal on the electrode. The deposition of additional metal is accomplished, for example, by electroplating the electrodes to selectively thicken them. Alternatively, small metallic pieces may be mechanically inserted into each via above each electrode, and these metallic pieces can be subsequently fused by heat or pressure in order to thicken the electrode at the microlocation. Such thickening of the electrode can enhance performance of the APEX by allowing tailoring of the contact surface, e.g., by selection of electrode metals such as gold. Also, the additional metal can enhance performance by effectively securing the metal layer to the substrate by fusing the electrode within the via.

The electrodes formed by exposure to the metal layer may be connected by metal traces to much larger contact pads located elsewhere on the first or second surface of the flexible polymeric substrate. When the electrodes are connected by vias to the circuit traces and contact pads printed on the second surface of the substrate, the first surface bearing the exposed electrodes can be directly laminated to a fluid handling architecture that directs the fluid sample to the electrode array. The contact pads on the second surface can be designed to extend to the edge of the device and mate directly with a voltage control unit by sliding the chip into a mated connector. This design overcomes arduous wire bonding processes of prior art APEX chips and overcomes the need to encapsulate the lead wires in a protective material, since they are shielded by the flexible polymeric substrate from exposure to the fluid sample.

The electrodes may be recessed within the vias in the flexible polymeric substrate and routed through conducting traces on the second surface of the flexible polymer substrate. Such a one-piece construction comprises a microwell above the electrode and provides protection for the circuit traces without the need for an additional protective layer. The microwell can serve as a reservoir for a sample or it can be partially or completely filled with a hydrophilic polymer to introduce a permeation layer or a biologically receptive gel above the electrode. In this manner the improved APEX device of the present invention overcomes the difficulties in mating a circuit board to a microwell array, as described in U.S. Pat. No. 5,605,662.

A hydrophilic permeation matrix on the top surface of the electrodes permits free-field electrophoresis of samples placed on the top surface of the APEX circuit while, at the same time, impeding the diffusion of large biomolecules, biologically receptive molecules, biologically reactive molecules, reagents or products through the matrix to the surface of the electrode. This matrix may be biologically receptive and used to attach biomolecules to the electrode. In certain implementations, a separate biologically receptive gel may be chemically or physically adhered to the permeation matrix or the electrode itself to support the attachment of biomolecules. The biologically receptive gel or permeation matrix may include an azlactone-functional monomer. As used in the present invention, "azlactone-functional monomer" means a monomer whose structure includes an azlactone moiety that optionally has been bound to a biomolecule by a ring opening reaction of the azlactone to form, e.g., an amide bond. The gel is preferably swellable, thereby providing an increased concentration of biologically receptive molecules per unit area when used as a coating. The biologically receptive gel may be configured and arranged such that it may be patterned to a high resolution. This gel may be cured by actinic radiation, and the cured composition may be capable of reacting with selective biomolecules to immobilize the biomolecules immediately above the micro-electrodes.

An azlactone-functional gel or permeation matrix can be employed and localized to the region just above the electrodes and within the confines of vias, in a specific embodiment of the invention. In this embodiment, some or all of the azlactone groups over a particular electrode can be reacted, through simple addition reactions, with selected amine- or thiol-terminated biomolecules to immobilize these biomolecules above the electrode, thus forming a biologically receptive gel. These selected biomolecules may be oligonucleotide or antibody probes, enzymes such as polymerase, or other biomolecules useful for analysis. One advantage of the azlactone based APEX films of the present invention is that the azlactone and the biomolecules can be anchored to the microlocations of the film by simple web coating, inkjet printing, or thermal imaging technologies, without the need for reagent additions or product removal, thereby greatly simplifying their manufacture relative to prior art APEX chips.

As used in the present invention, "hydrophilic permeation matrix" is a polymeric material capable of swelling in water, such as by adsorption or chemical interaction, and refers to the matrix material either before or after swelling in water. "Photocrosslinker" means a chemical species that is capable of binding two or more polymer molecules in response to the application of electromagnetic radiation. The photocrosslinker is capable of attaching to the polymer molecules at a site other than the end of a growing polymer chain. "Copolymeric crosslinker" means a chemical species that is capable of binding two or more polymer molecules, and that attaches to a polymer at the end of a growing polymer chain.

As used herein, "biologically active" includes biochemically, immunochemically, physiologically, or pharmaceutically active; and "biologically active molecule" and "biomolecule" are used interchangeably and include antibodies, antigens, enzymes, cofactors, inhibitors, hormones, receptors, coagulation factors, amino acids, histones, vitamins, drugs, cell surface markers, carbohydrates, proteins and polypeptides, DNA (including DNA oligonucleotides), RNA (including RNA oligonucleotides), and derivatives of the foregoing. "Substituted" means substituted by conventional substituents which do not interfere with the desired product, e.g., substituents can be alkyl, alkoxy, aryl, phenyl, halo (F, Cl, Br, I), cyano, nitro, etc.

The invention provides a flexible polymeric substrate that can be continuously produced on a commercial scale in the convenient form of a roll-good that can be readily stored and handled. The finished roll-good can be used directly after application of the hydrophilic matrix or biologically active gel to perform electrophoresis assisted processing of chemical, biological, or particulate materials at electronically addressed micro-locations. For example, the flexible polymeric substrate can be used on a spool or roll-good in a continuous reel-to-reel process in which a plurality of addressable programmable electrode matrices are sequentially supplied, used, and taken up. Alternatively, the roll-good can be cut into sections containing a plurality of APEX arrays for incorporation into biocards. Also, alternatively, the roll-good may be cut into separate APEX units for individual use. It will be appreciated that the flexible polymeric substrate containing the APEX unit or units can further include or be combined with other microelectronic, microoptical, microstructural, and/or micromechanical elements. These microelements may be incorporated into multilayer articles.

The invention is further directed to a multi-sample APEX processing spool and system in which the first surface of a roll of the APEX film may be laminated to a flexible plastic fluid handling architecture, said fluid handling architecture designed to direct 2–10,000 independent biological samples to the corresponding number of independently addressable APEX arrays on the APEX film for processing. The spool can be advanced through a machine that injects a sample into a subset of the APEX arrays for processing. Once the samples are assayed, the spool can be advanced, exposing additional APEX arrays. A voltage control unit simultaneously can provide processing currents or voltages to each of the APEX arrays on the spool at any one time. A detection system can provide optical, electrical, or mechanical signals in response to the biological events at the individual electrodes of each APEX array. Thus, continuous automated processing, whether sequentially or simultaneously, of thousands of samples can be carried out using inexpensive, disposable arrays.

The invention is further directed to a multi-sample APEX biocard and system in which a sheet of APEX film may be laminated to a semi-rigid glass or plastic fluid handling architecture, said fluid handling architecture designed to direct numerous independent biological samples to the corresponding number of independently addressable APEX arrays on the APEX film for processing, preferably between 2 and 200 samples. The fluid handling architecture can be anything from simple barriers between APEX arrays, including open wells into which sample is injected when the cassette is horizontal, to closed channel structures into which a sample is injected with a syringe or pump. A machine can be adapted to accept and operate the APEX cassette. The machine may comprise a sample injection unit to provide numerous (preferably from 2 to 200) independent biological samples onto the biocard via ports in the fluid handling architecture; a voltage control unit that can simultaneously provide processing currents or voltages to each of the APEX arrays; and a detection system that can provide optical, electrical, or mechanical signals in response to biological events at the individual electrodes of each APEX array.

The invention is further directed to a method of performing molecular biological processes, the method including providing an electronic device containing a flexible polymeric substrate having a first surface and a second surface. The electronic device may comprise an array of electrodes disposed on the first or second surfaces of the flexible substrate and exposed toward the first surface. A hydrophilic permeation matrix and biologically receptive polymer having a covalently anchored biological molecule can be positioned on the first surface of the flexible substrate such that they are in contact with the array of electrodes, after which an electrical force can be applied to the electrodes so as to effect electrophoresis-assisted processing of the biological sample. By similar means, electrophoretic processing of chemical or particulate matter also can be envisioned.

In specific implementations of the method of the invention, the electronic device may include a plurality of electrodes. The charge potential of the electrodes preferably can be individually controllable. Alternatively, the charge potential of the electrodes can be controlled together as one unit, or as a group of sub-units, each sub-unit having a plurality of electrodes electronically coupled to one another. During operation, the charge potential of the electrodes optionally can be altered in order to modify the electrical field of the electronic device. Such alterations to the electrical field can be used, for example, to first attract all the charged biologically active molecules to the biologically receptive gel, and then to subsequently repel the biologically active molecules that are not retained by the receptive gel. These efforts can result in accumulation of desired biomolecules and removal of undesired molecules from the positions of the electrodes based on specific biomolecular recognition by anti-body or oligonucleotide probes associated with the individual microelectrodes.

Other features and advantages of the invention will be apparent from the following detailed description of the invention and the claims. The above summary of principles of the disclosure is not intended to describe each illustrated embodiment or every implementation of the present disclosure. The figures and the detailed description that follow more particularly exemplify certain embodiments utilizing the principles disclosed herein.

BRIEF DESCRIPTIONS OF THE DRAWINGS

Principles of the invention may be more completely understood in consideration of the detailed description of various embodiments of the invention that follows in connection with the accompanying drawings in which.

FIGS. 8A, 8B, 8C, 8D, and 8E are partial cross-sectional views of an APEX circuit manufactured on a flexible polymeric substrate, showing the APEX circuit during various steps of manufacture.

Figure 9:
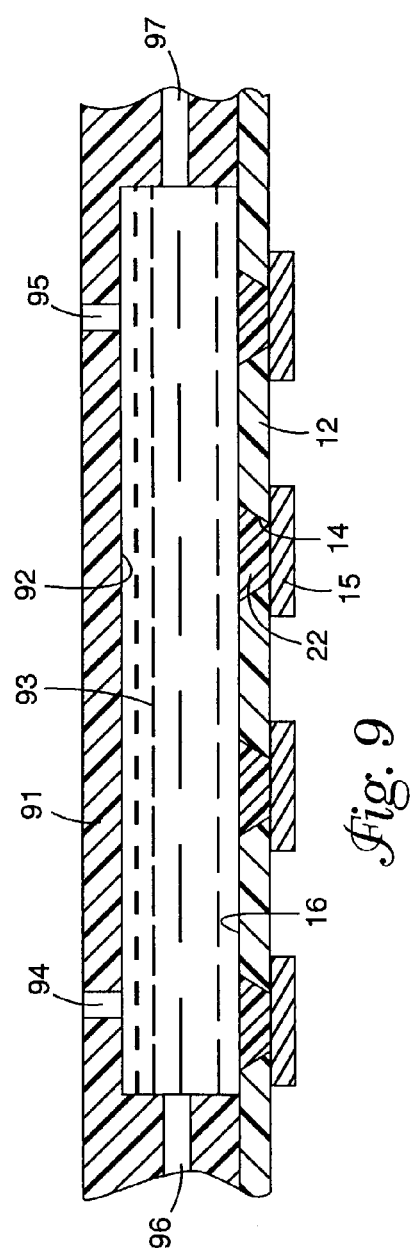

FIG. 9 is a cross-section view of an APEX circuit including a fluid-handling architecture in accordance with another implementation of the invention.

Figure 10A:
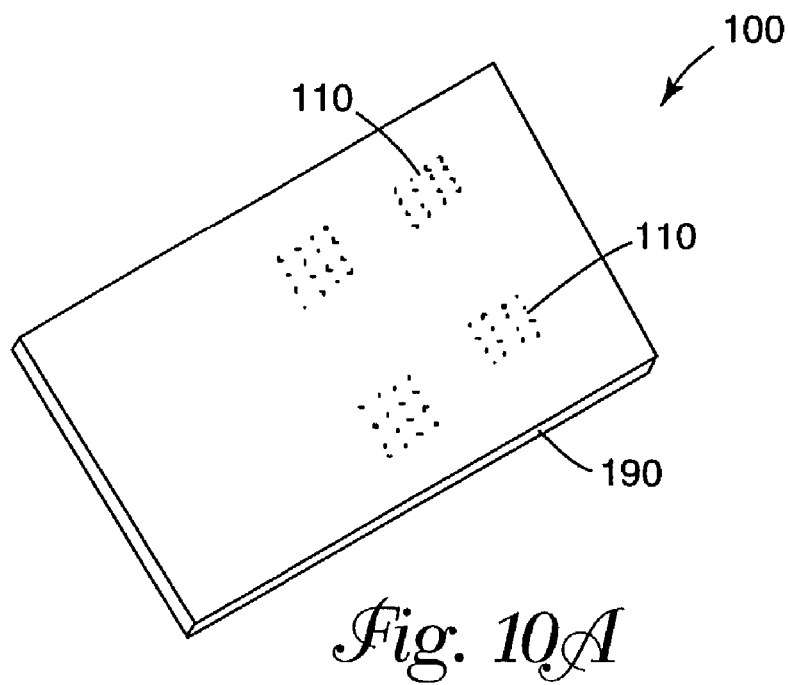
Figure 10B:
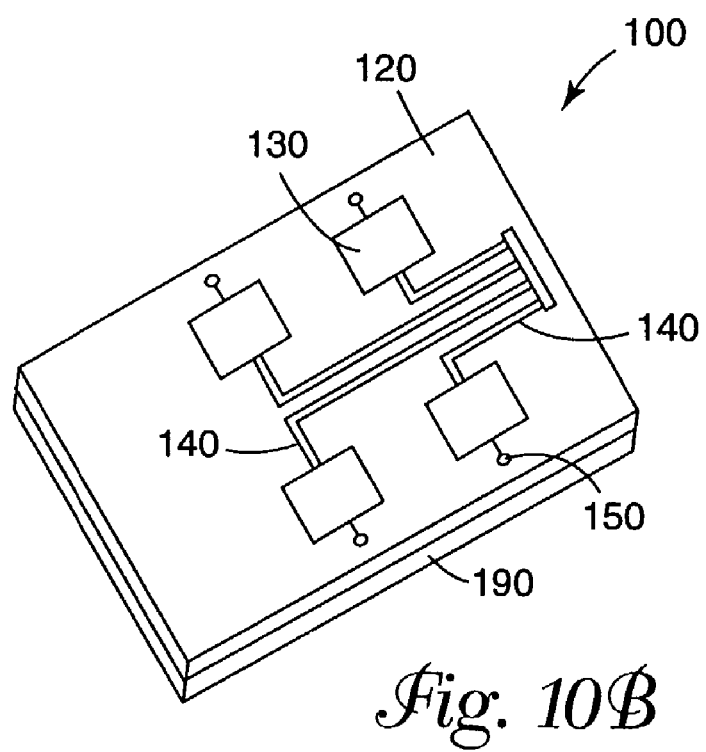

FIGS. 10A and 10B is are perspective views of a biocard in accordance with an implementation of the invention.

Figure 11:
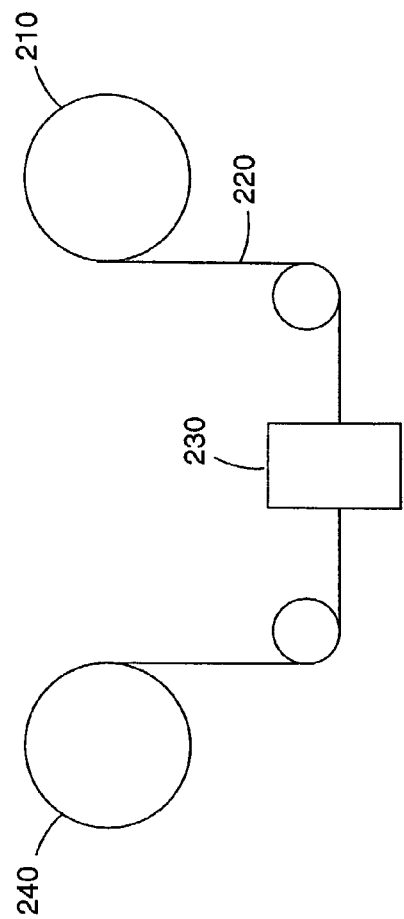

FIG. 11 is a schematic representation of the roll-to-roll process of the invention.

While principles of the invention are amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION OF THE INVENTION

The present invention provides an electronic device adapted for processing chemical, biological, or particulate materials at electronically addressed microlocations. In specific implementations, the device includes a flexible polymeric substrate having a first surface and a second surface. The first surface is preferably oriented upward when in use, and the second surface is preferably oriented downward. A plurality of microlocations interrupts the first surface, and each of these microlocations preferably includes an electrode disposed on the first or second surfaces of the flexible substrate.

The flexible polymeric substrate allows the electronic device to be manufactured in a continuous, roll-to-roll, mass-produced manner, free of the inherent limitations experienced by electronic devices manufactured batch-wise on silicon substrates. In addition, the flexible polymeric substrate allows the electronic device to be manufactured and stored as a spool or roll-good. This roll-good can contain a plurality of independent electronic devices that are separated from one another during use or which are used sequentially while on the roll.

A hydrophilic permeation matrix and optionally a biologically receptive gel is positioned on the first surface of the flexible substrate and is capable of electrical contact with the individual electrodes. In particular embodiments, the permeation matrix and biologically receptive gel are localized on the individual microlocations. The permeation matrix permits free-field electrophoresis of macromolecules and particles while preferably impeding their diffusion to the surface of the electrode, where they might foul the electrode or undergo electrochemical reactions. The biologically receptive gel permits the covalent binding of biomolecules such as DNA probes, antibodies, enzymes, and the like, useful for processing of chemical, biological, or particulate materials near the electrode surface. In one implementation of the invention, the matrix and gel permit the isolation of biological targets, such as DNA fragments, antigens, and other biologically active molecules.

During operation of the invention in certain embodiments, a small quantity of test liquid containing a mixture of biological target species is applied to the APEX array. A biasing signal (voltage or current) is applied to selected electrodes, thereby accelerating transport of the target species into the hydrophilic matrix above the selected electrodes. The biasing voltage is subsequently stopped, with the target species concentrated at one or more of the microlocations. If biomolecular probes are present at the microlocations, the selected test species specifically hybridize or otherwise interact with the biomolecular probes, while other test species not specifically recognized by the probes are free to diffuse back into solution. Optionally, a reverse voltage bias is applied to the electrodes to quickly remove all unhybridized species from the microlocations.

This process can be repeated at different microlocations, such that a test species is moved from one microlocation to another until it reaches the microlocation having a probe specific to that species, and becomes bound there. The presence or absence of the target species is then determined using conventional identification methods, such as measuring the fluorescent signature for a reporter species attached to the selected target species at each microlocation.

In other embodiments, the microlocations can be configured to serve as sites for chemical reactions. For example, an enzyme can be covalently anchored at a microlocation. A biasing signal can be applied to that microlocation to direct an enzyme substrate to that microlocation, where the enzyme can act upon the substrate. By reversing the bias, products of the enzymatic reaction can be driven away from the electrode, or redirected to a different electrode based on free field electrophoretic transport.

Figure 1:
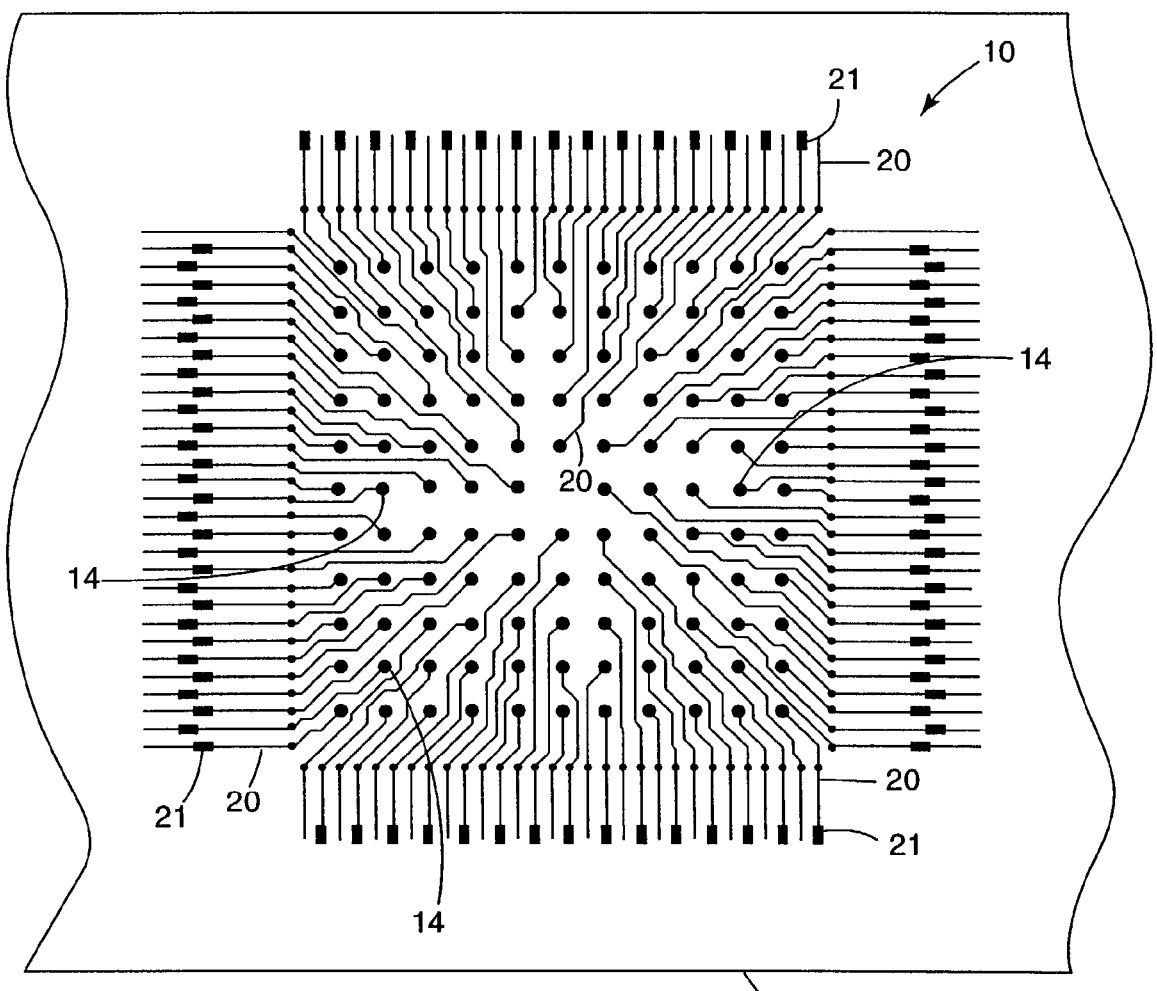
FIG. 1 is a bottom plan view of an APEX circuit constructed in accordance with the present invention.
Figure 2A:
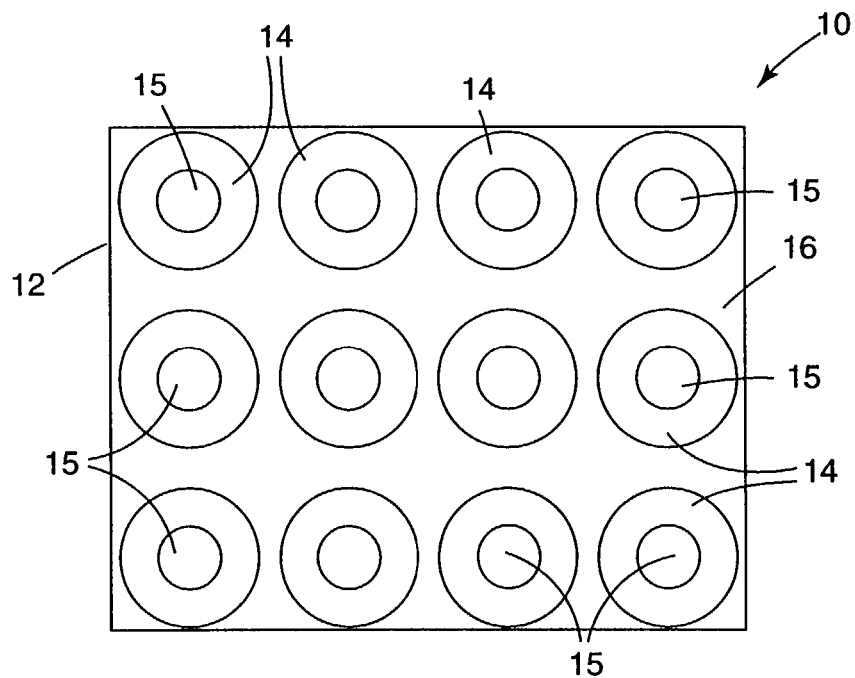
FIG. 2A is an enlarged top view of a flexible polymeric substrate containing an APEX circuit constructed in accordance with the present invention, showing microwell locations.
Figure 2B:
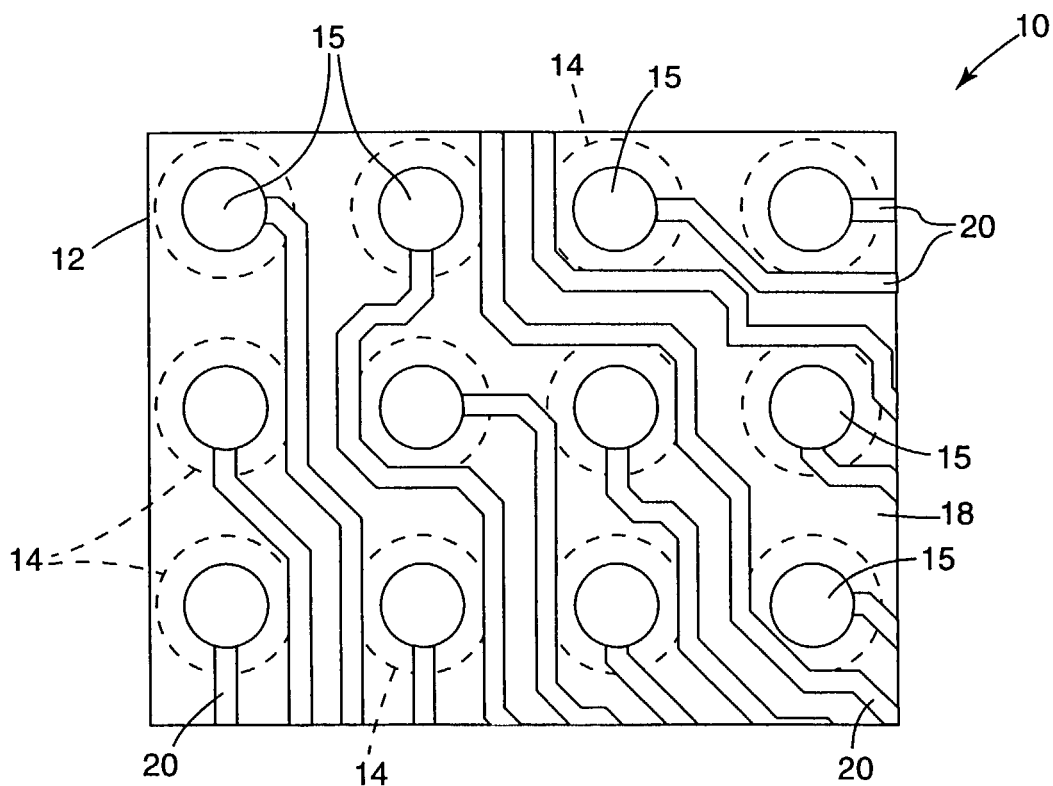
FIG. 2B is an enlarged bottom view of the flexible polymeric substrate depicted in FIG. 1, showing the bottom of the APEX circuit constructed in accordance with the present invention, including electrical contact points.

To more fully illustrate the invention, reference is now made to the figures, which show various implementations of electronic circuits constructed in accordance with the present invention. FIG. 1 is a bottom plan view of an addressable programmable electrode matrix (APEX) circuit 10 constructed on flexible polymeric substrate 12. Circuit 10 includes numerous microelectrodes that are connected by metal traces 20 to individually addressable contact pads 21, which may in turn be connected to current or voltage control circuitry (not shown). In this embodiment, microelectrodes extend through the flexible polymeric substrate from bottom surface 18 to top surface 16 to define corresponding microlocations 14 on top surface 16 of substrate 12 (shown in FIGS. 2A and 2B). Details of APEX circuit 10 are more clearly shown in FIGS. 2A and 2B. FIG. 2A is an enlarged top plan view of a portion of APEX circuit 10 constructed on flexible polymeric substrate 12. APEX circuit 10 has a plurality of microlocations 14 in polymeric substrate 12, comprising metal electrodes 15. FIG. 2B is an enlarged bottom plan view of a portion of APEX circuit 10 depicted in FIG. 2A, showing bottom surface 18 of flexible polymeric substrate 12, along with metal traces 20 terminating in metal electrodes 15 located in microlocations 14. In the implementation depicted, each metal trace 20 connects to a different microlocation 14 and includes a contact pad 21 (shown in FIG. 1). In use, metal traces 20 are in electrical contact with a voltage source by way of contact pad 21 that permits the creation of a biasing voltage across each of the electrodes. It will be appreciated that in certain implementations the biasing voltage at each electrode is individually controllable and distinct from the other electrodes. However, in other implementations, the electrodes are controlled as one or more groups.

Figure 3:
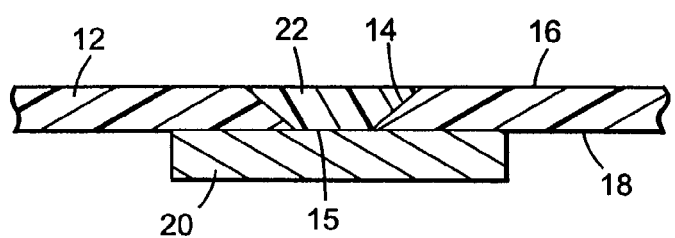
FIG. 3 is a fragmentary cross-sectional view of a flexible polymeric substrate and an electrode constructed in accordance with an implementation of the invention.

FIG. 3 is a side cross-sectional view of APEX circuit 10 constructed on flexible polymeric substrate 12 shown in FIG. 2A and FIG. 2B. Hydrophilic permeation matrix 22 is positioned on the individual microlocation 14 and may extend onto the top surface 16 of the flexible polymeric substrate 12. In the embodiment depicted, metal trace 20 is depicted on bottom surface 18 of flexible polymeric substrate 12. Although permeation matrix 22 is localized to the area of the microlocation 14 corresponding to an electrode 15, it will be appreciated that in certain implementations permeation matrix 22 covers the entire top surface 16 of polymeric substrate 12. It will also be appreciated that in other certain implementations permeation matrix 22 is localized to the area of the microlocation 14 and may be of a thickness different than that of the flexible substrate 12.

Figure 4A:
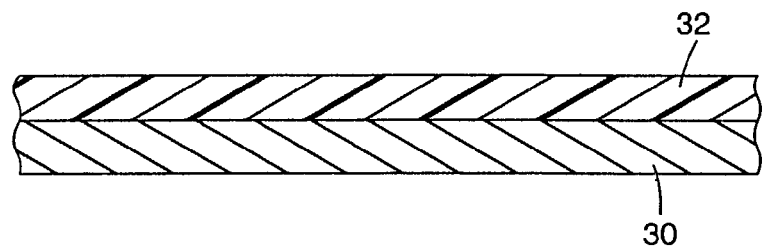
FIGS. 4A, 4B, 4C, 4D and 4E are fragmentary cross-sectional views of an APEX circuit manufactured on a flexible polymeric substrate, showing the APEX circuit during various steps of manufacture.
Figure 4B:
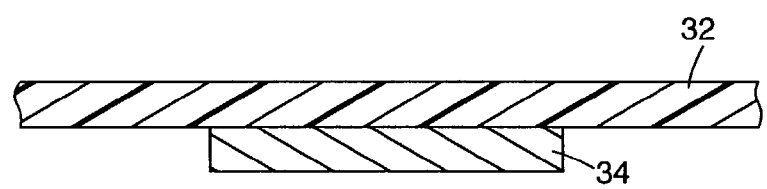
Figure 4C:
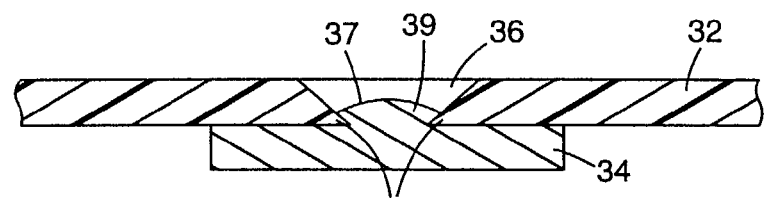
Figure 4D:
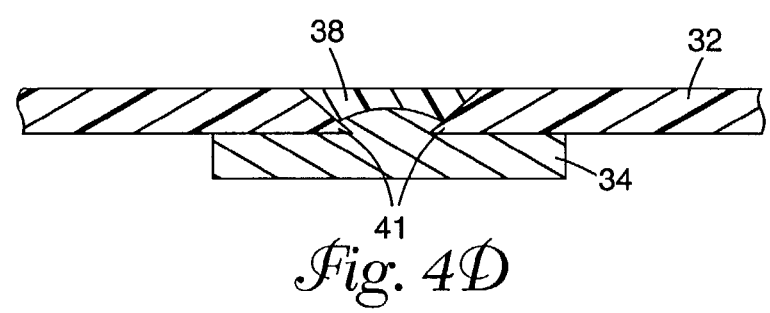
Figure 4E:
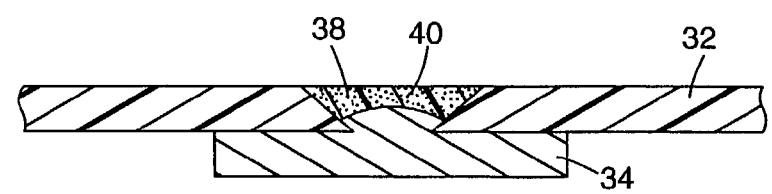

APEX circuit 10 may be manufactured using various methods and materials, according to the method disclosed in U.S. Pat. No. 5,401,913 (Columns 3, 4, and 5, and FIGS. 1–7), the teachings of which are incorporated herein by reference in their entirety. In reference now to FIGS. 4A, 4B, 4C, 4D, and 4E, one implementation is depicted. As shown in FIG. 4A, metal layer 30 is deposited on a surface of flexible polymeric substrate 32. Using conventional methodologies, metal layer 30 is subsequently patterned and etched in order to form a plurality of metallic traces 34, one of which is shown in cross-sectional view in FIG. 4B. After metal traces 34 have been formed on flexible polymeric substrate 32, portions of substrate 32 are removed or "milled" away from each of the electrodes to form vias 36 over each electrode 37, as shown in FIG. 4C, thereby exposing bare metal. Removal of substrate 32 can be performed by methods known in the art, including chemical, plasma, and laser processes. In the embodiment depicted, the bare metal of metal trace 34 has been expanded at the location of electrode 37 by deposition of additional metal to create protrusion 39. Protrusion 39 ensures better conductivity by increasing the surface area of electrode 37, and also provides for better adhesion of the metal trace 34 by forming lip 41 that slightly overlaps and interlocks with substrate 32. After via 36 has been formed, and protrusion 39 on electrode 37 created, hydrophilic matrix 38 is applied, which coats electrode 37 and optionally fills via 36, as shown in FIG. 4E. Finally, appropriately defined microlocation 40 of matrix 38 is doped with an appropriate receptor capable of determining a chemical signature of various test-species, as shown in FIG. 3E.

Figure 5:
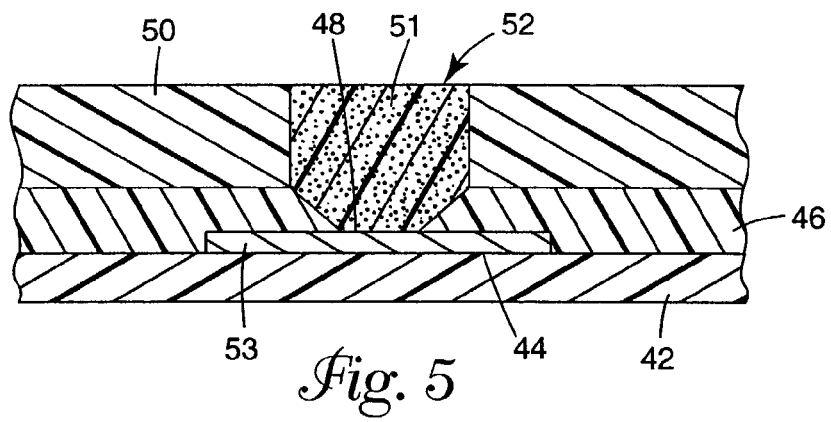
FIG. 5 is a partial cross-sectional view of a flexible polymeric substrate and electrode constructed in accordance with another implementation of the invention.

In reference now to FIG. 5, another configuration for an electrode in an APEX array is depicted in cross-sectional partial view. In FIG. 5, microlocation 52 is first formed by depositing conducting metal 53 on flexible polymeric substrate 42. Suitable metals include aluminum, gold, silver, tin, copper, palladium, platinum, carbon and various metal combinations. Special techniques for assuring the proper adhesion to the insulating polymer substrate (e.g., polyimide or polyester) are used with different metals. The conducting metal is selectively removed to form a plurality of traces 44, one of which is shown in FIG. 5. After formation of trace 44, non-conducting masking layer 46 is applied over flexible polymeric substrate 42 such that it covers and substantially obscures metal trace 44. Non-conducting masking layer 46 is preferably also constructed of a flexible material that is capable of flexing along with polymeric substrate 42. Non-conducting masking layer 46 is subsequently milled and partially removed in order to reveal metal trace 44, thereby forming electrode 48. After forming electrode 48, matrix 50 is deposited over the top of masking layer 46. In the embodiment shown, matrix 50 entirely covers non-conducting masking layer 46. However, in other embodiments, matrix 50 may cover only a portion of masking layer 46 or it may cover only the electrode 48. Thereafter portion 51 of matrix 50 is doped with, for example, receptor molecules at microlocation 52.

Figure 6:
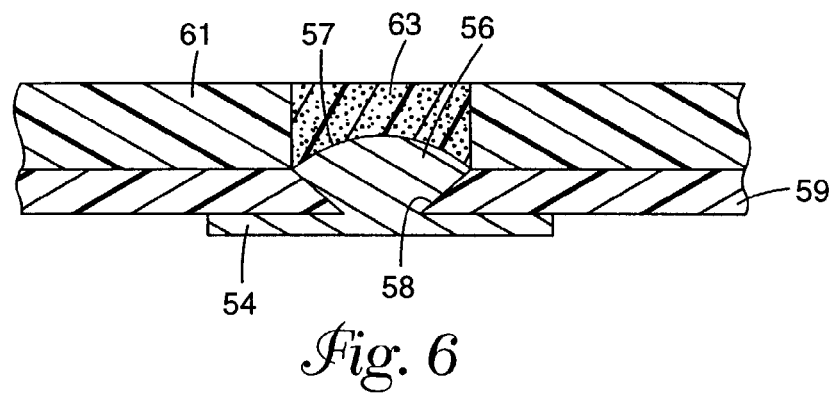
FIG. 6 is a partial cross-sectional view of a flexible polymeric substrate and electrode constructed in accordance with another implementation of the invention.

Yet another implementation of the invention is shown in FIG. 6, which depicts electrode 57 in which metal trace 54 has been enlarged to create raised area 56 projecting into via 58 formed in polymeric substrate 59. Electrode 57 is enlarged by deposit of metal. This deposit is formed, for example, by electroplating electrode 57 to selectively thicken the top surface thereof. Alternatively, small metallic pieces may be mechanically inserted into each via above each electrode 57, and these metallic pieces can be solder re-flowed to create raised area 56. Such thickening of electrode 57 can enhance performance of the APEX array by creating a larger, more uniform electrode. In addition, raised area 56 can enhance performance by effectively securing the metal layer to the substrate. After forming electrode 57, matrix 61 is deposited over the top of substrate 59. In the embodiment shown, matrix 61 entirely covers substrate 59. However, in other embodiments, matrix 61 may cover only a portion of substrate 59 or only the electrode 57. Thereafter portion 63 of matrix 61 is doped with, for example, receptor molecules.

Figure 7:
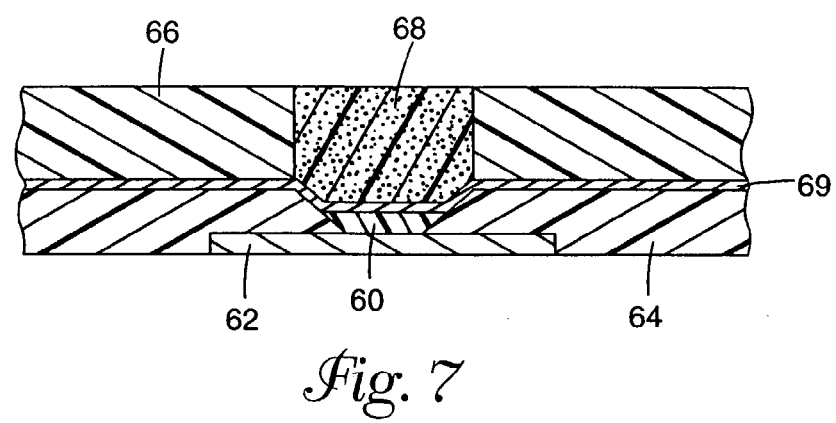
FIG. 7 is a partial cross-sectional view of a flexible polymeric substrate and electrode constructed in accordance with another implementation of the invention.

FIG. 7 shows yet another implementation of the present invention, in which electroresistive layer 60 is shown positioned over electrode 62. FIG. 7 also shows flexible polymeric substrate 64, matrix 66, and matrix portion 68 that has been doped with, for example, receptor molecules. In addition, common ground plane 69 is placed over the top of electroresistive layer 60 and substrate 64. Ground plane 69 allows electrical conduction from electrode 62, through resistive layer 60, and then into ground plane 69. Due to the electrical resistance in electroresistive layer 60, the temperature of gel portion 68 above the electrode can be increased and controlled. If each of the electrodes in the APEX circuit is individually controlled, the temperature of each of the electrodes can also be individually controlled. It will be appreciated that the resistive layer can be associated with the electrode in different configurations, including positioning the electrode between the resistive layer and the gel.

Figure 8A:
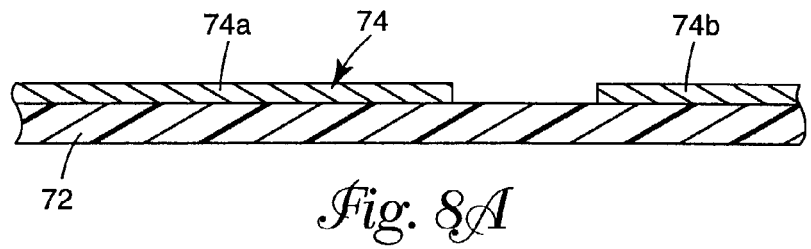
Figure 8B:
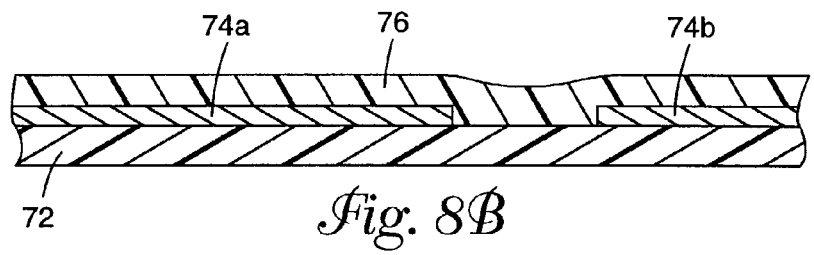
Figure 8C:
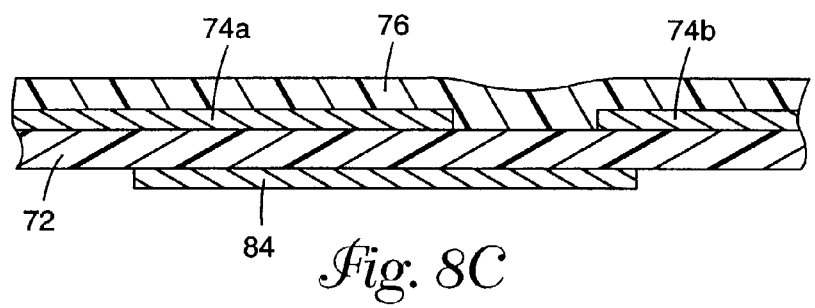
Figure 8D:
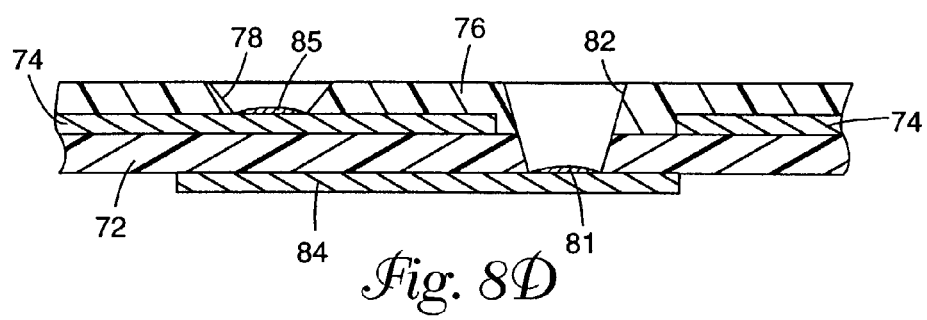
Figure 8E:
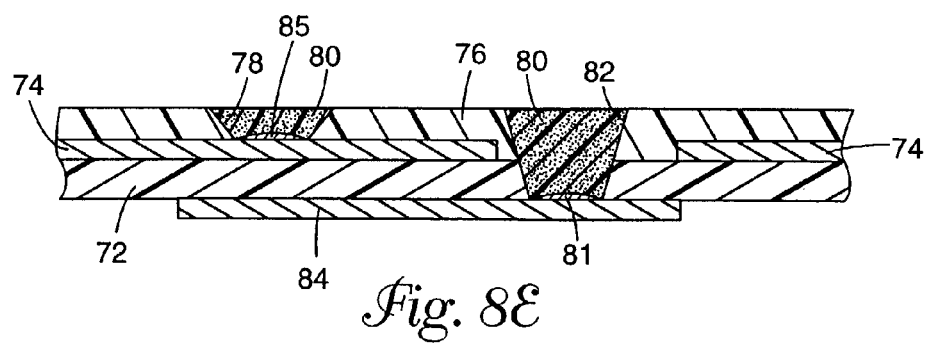

The embodiments depicted above show single-layer substrates with one layer of metal traces. However, it will be appreciated that the substrate can have more than one layer. In addition, the metal traces may be positioned on one or more layers, depending upon the dictates of the application. For example, FIGS. 8A–8E show the steps of manufacture of yet another APEX circuit, and a cross-sectional view of a portion of a finished APEX circuit. In FIG. 8A, flexible polymeric substrate 72 is shown with metal layer 74, depicted as two separate traces 74a and 74b. Traces 74a and 74b may be formed from a single layer of metal by using conventional etching methodologies. After forming separate traces 74a and 74b, masking layer 76 is applied over the traces, as shown in FIG. 8B. Independent electrode 81 is formed by deposition of additional metal trace 84, as depicted in FIG. 8C. Thereafter, masking layer 76 and substrate 72 can be etched to form vias 78 and 82, after which additional metal may be electrodeposited to form electrodes 81 and 85 as shown in FIG. 8D. Vias 78 and 82 are subsequently filled with hydrophilic matrix 80, which may be, for example, an aziactone-bearing polymer, as depicted in FIG. 8E. In implementations where high electrode density is desired, the metal traces are preferably layered in order to allow more electrodes to be positioned in a specific surface area.

In use, the array of microlocations 14 is brought into contact with a single fluid volume that contacts top surface 16 but does not contact bottom surface 18. By applying electrical currents or voltage via contact pads 21, free field electrophoresis can be controlled at each microlocation 14. The single fluid volume can be a free-standing liquid (e.g., an aqueous buffer solution held in place by contact angle to hydrophobic flexible polymer substrate 12. Alternatively, as shown in FIG. 9, the single fluid volume can be defined by contacting top surface 16 with fluid handling architecture 91 that is designed to confine a specified volume of sample-containing fluid as single fluid volume 93 over the array of microlocations 14. The enclosed volume over the array of microlocations 14 can be defined as APEX sample chamber 92. Fluid handling architecture 91 can be designed to provide at least one inlet port 94 and/or one outlet port 95 to allow a fluid sample to be transported into APEX sample chamber 92 for subsequent analysis. Optionally, fluid handling architecture 91 can provide for more than one APEX sample chamber 92 that can be mated to more than one array of microlocations 14. Sample chambers thus formed can be fluidly connected by inlet ports 96 and/or outlet ports 97 in the form of microchannels, microtubing, micropipettes, and the like.

In all of the embodiments, the flexible polymeric substrate is preferably flexible enough such that it may be bent around a mandrel of 2 feet in diameter without significant loss of integrity of the electrical circuits. More preferably the flexible polymeric substrate may be bent around a mandrel 1 foot in diameter, and most preferably bent around a mandrel 6 inches in diameter, without significant loss of integrity of the circuits.

In certain implementations of the invention, the flexible polymeric substrate is comprised completely, primarily, or partially of polyimide. Other flexible substrate materials may also be used, including poly(methylmethacrylate), polycarbonates, polyolefins, polyamides, polyvinyl chloride, and polytetrafluoroethylene, polyesters, or epoxies. Other ingredients which may be incorporated into the substrate include plasticizers, toughening agents, pigments, fillers, stabilizers, antioxidants, flow agents, bodying agents, leveling agents, colorants, binders, fungicides, bactericides, surfactants, glass and ceramic beads, and reinforcing materials such as woven and non-woven webs of organic and inorganic fiber, provided that none of the added ingredients interfere with the chemical or biochemical processes for which the APEX array is intended.

In certain implementations, the biologically receptive gel includes an azlactone-functional monomer. The gel advantageously is swellable, thereby providing an increased concentration of biologically receptive molecules per unit area when used as a coating. The biologically receptive gel is configured and arranged such that it may be patterned to a high resolution. This patterned biologically receptive gel may be cured with actinic radiation, and the cured composition is capable of reacting with selective biomolecules to immobilize the biomolecules immediately above the microelectrodes. High-resolution patterning of azlactone-functional gels, including gels containing biologically active materials, is described in applicant's copending U.S. patent application Ser. No. 09/183197, filed Oct. 30, 1998, the teachings of which are incorporated herein by reference in their entirety.

One preferred procedure for the derivitization of the metal micro-electrode of the present invention uses aminopropyltriethoxysilane (APS) as a permeation and/or primer layer. APS reacts readily with the oxide and/or hydroxyl groups on metal surfaces to provide a high level of functionalization, with only very limited binding to the remaining polymer substrate. This primer will support the transport of small ions and water as required to sustain electrophoresis, while impeding the diffusion of larger biomolecules. In addition, through a simple addition reaction to the APS primer film, the amine groups in the primer can be reacted with azlactone functional polymers to introduce a functional hydrophilic matrix above the electrodes. This azlactone polymer can be configured with photocrosslinkers that enable the polymer to be photolithographically patterned into gel pads at each microlocation. This azlactone functional gel contains additional functional groups that can be hydrolyzed to carboxylic acids, giving a hydrophilic gel. The resulting patterned array of azlactone-functional gel pads, one on each microlocation of the roll-good, can be reacted with biomolecules by a simple and quantitative addition reaction that does not require co-reagents or removal of unwanted side products. Therefore, a roll-good of the present invention can be doped with biomolecules by selectively printing using a standard inkjet, flexographic, or other printing methods. This overcomes the very tedious prior art process of using free-field electrophoresis to direct the covalently attachable biomolecules to individual microlocations in preparation for covalent attachment.

The azlactone-functional monomer may be any suitable monomer containing an azlactone function group. A co-monomer may also be included, and the co-monomer may be any suitable monomer. Preferred monomers include vinyl group-containing and acryl group-containing compounds. A representative list of such monomers includes acrylamide, methacrylamide, N,N-dimethylacrylamide, diacetoneacrylamide, N-vinylpyrrolidone, hydroxyethyl methacrylate, 2-acrylamido-2-methylpropanesulfonic acid and its salts, N-(3-methacrylamidopropyl)-N,N,N-trimethylammonium salts, N,N-dimethylaminoethyl methacrylate, acrylic acid, methacrylic acid, itaconic acid, and combinations thereof. Preferred co-monomers are N,N-dimethylacrylamide and N-vinylpyrrolidone.

An example of a lithographically patternable azlactone functional polymer useful in the preparation of APEX chips is a copolymer prepared from equal amounts of vinyldimethylazlactone with dimethylacrylamide. This polymer composition can be reacted with a heterodifunctional photocrosslinker that has an amine functional group that binds to the azlactone, and an azido functional group that forms a crosslink to another polymer chain upon application of UV light. This material is thermally reacted with the APS modified electrode surface to provide a covalent attachment to the electrode. The material is then lithographically photocrosslinked to create individual gel pads at each microlocation, and excess material is removed. Each gel pad has residual azlactone functionality that can then be hydrolyzed or selectively reacted with thiol- or amine-terminated biomolecules specific to that microlocation.

Optional copolymeric crosslinkers may be included in the gel. These crosslinkers may be any suitable species with two or more polymerizable functions.

Suitable multifunctional crosslinking monomers include ethylenically unsaturated trimethylolpropane triacrylate and trimethacrylate, (alpha-unsaturated) esters such as ethylene diacrylate and ethylene dimethacrylate, and amides, such as N,N'-dimethacryloyl-1,2-diaminoethane, and reaction products of 2-alkenyl azlactones with short chain diamines.

The photocrosslinker may be any suitable chemical species that is capable of binding two or more polymer molecules in response to the application of electromagnetic radiation and that is capable of attaching to the gel-forming polymer at sites other than the end of a growing polymer chain. The photocrosslinker should be capable of attaching to the polymer after polymerization of the polymer is complete. Preferred photocrosslinkers include bisazides, bisdiazocarbonyls, and bisdiazirines. The bisazides are most preferred with regard to ease of use. Azide ($-N_3$) groups release nitrogen ($N_2$) upon application of UV light, leaving behind highly reactive divalent nitrogen, i.e., nitrene. Reactive carbene can be generated by photolysis of a diazocarbonyl or a diazirine. Active nitrene or carbene species can insert into many types of bonds including C—C or C—H bonds on pre-polymerized polymers to provide a crosslink. Azide, bisazide, azocarbonyl and bisdiazocarbonyl crosslinkers may form substrate-to-polymer gel links as well as polymer gel-to-polymer gel crosslinks, and are therefore preferred. Preferred diazide species include 2,6-bis(4-azidobenzylidene)-4-methyl cyclohexanone (3AMC), 4,4'diazidodiphenylether, 4,4'diazidodiphenylsulfone, 4,4'diazidodiphenyl acetone, and 4,4'diazidodiphenylmethane. Preferred bisdiazocarbonyl species include 4,4-bis(m-diazobenzyl) benzene. The photocrosslinker may be capable of thermal cure as well as photocure.

In another implementation, the photocrosslinker may be a hetero-difunctional compound having a first function which attaches to the polymer and a second function which forms crosslinks upon application of light. For example, 4-[p-azidosalicyamido]butylamine (ASBA, available from Pierce Chemical Co., Rockford, Ill.) has an amine function that binds to an azlactone, and an azido function that forms a crosslink to another polymer chain upon application of UV light, as described above.

In cases where the photocrosslinker attaches to the polymer by occupying an azlactone function of the polymer, the crosslinker must be present in an amount less than 1 equivalent so that it does not occupy all of the azlactone sites necessary to bind biomolecules. In other words, the number of azlactone-reactive functions present on photocrosslinkers must be less than the total number of azlactone functions present on the polymer. However, if the biomolecules are attached prior to photocrosslinking, i.e., the composition already contains biomolecule-azlactone bonds, then this condition need not apply.

The gel composition may be coated onto the flexible substrate, cured (i.e., photocrosslinked), patterned, and reacted with biomolecules. By varying methods, these steps may be done in any order. Many techniques, such as photolithographic patterning and laser induced thermal imaging (LITI) patterning, involve simultaneous or near-simultaneous steps selected from coating, curing, or patterning of the composition. A preferred approach to patterning gel pads onto the microlocations of the APEX film is by LITI, because of the high registration accuracy achievable by this process. Specifically a high spot placement accuracy across the web can be achieved for precisely transferring gel pads from a donor sheet onto the micro-locations on the web of APEX arrays.

Coating of the composition on the substrate may be achieved by any suitable method. The coating may have a thickness in the range of 20 to 500 μm, but is preferably between 0.05 and 100 μm and most preferably between 1 and 20 μm. The composition may be coated with or without addition of solvent. Suitable methods include spin coating, spray coating, knife coating, dipping, or roller coating. The composition may be selectively coated to provide a patterned surface. Such methods include known printing methods such as ink jet printing, offset, flexographic printing, etc. The composition may also be knife coated onto a microstructured surface (e.g., a surface having micron scale depressions or channels) in such a way that the composition resides only in the microstructures, providing a patterned array of the composition.

The gel may be cured by exposure to electromagnetic radiation, preferably UV light, most preferably UV-A light. The gel may be selectively cured by selective exposure to light. Selective exposure methods include exposure through a mask or photographic negative or exposure by a directed beam of light or laser. Uncured gel may then be removed, e.g., by washing, to provide a patterned coating. The gel may then be further cured, either by light or heat cure. Heat cure may entirely replace light cure in some circumstances, in particular where the gel is not patterned or is patterned by means other than photopatterning, such as by mechanical means.

Patterning may be achieved by a variety of means including selective coating of the gel on a substrate, selective curing of the gel, or selective removal of the gel from a substrate. It is an advantage of the present invention that the gel may be photopatterned to a resolution of less than 2 micrometers by selective curing of the gel. Typical features are less than 1000 micrometers in size. Preferably, the patterned coating has features of less than 200 µm in size. Preferably, the patterned coating should cover the electrode surface 14. The size dimensions referred to above are in-plane dimensions of the coated features or of the interstices between the coated features.

The doped gel may be patterned onto a substrate by laser addressable thermal transfer imaging (e.g., laser induced thermal imaging, or LITI) processes such as those described in U.S. Pat. No. 5,725,989, incorporated herein by reference. In this process, a thermal transfer donor element is constructed comprising a support layer, a light-to-heat conversion layer, and a transfer layer comprising the composition to be patterned. When the donor element is brought in contact with a receptor and selectively irradiated to form a pattern or an image, a melt stick transfer process occurs and the composition containing transfer layer is imaged onto the receptor. The photocrosslinkable azlactone composition of this invention can be used in the transfer layer of such a system. This photocrosslinkable azlactone composition can be reacted with biomolecules before incorporation into the transfer layer, after incorporation into the transfer layer, or after laser addressed thermal transfer to the receptor. The azlactone composition of this invention can be thermally or photochemically crosslinked before or after the transfer process.

This process offers the opportunity to pre-pattern different biomolecules onto a transfer layer comprising the present azlactone composition prior to laser addressed thermal imaging of individual azlactone-biomolecule conjugates to the receptor substrate. Registration of the elements may be robotically altered between any or all of the transfer steps to build up desired array spacing and size for transferred elements on the receptor that is different from the patterning of the biomolecules on the transfer layer. The laser addressable thermal imaging process offers high resolution imaging and high registration accuracy.

The azlactone functions of the doped polymer may bind to a variety of attaching functions present on biomolecules, including, primary amine, secondary amine, hydroxy and thiol. These groups react, either in the presence or absence of suitable catalysts, with azlactones by nucleophilic addition to produce a residue of a biomolecule bound to a residue of an azlactone function.

Depending on the attaching function of the biomolecule, catalysts may be required to achieve effective attaching reaction rates. Primary amine or thiol functions require no catalysts. Acid catalysts such as trifluoroacetic acid, ethanesulfonic acid, toluenesulfonic acid, and the like are effective with hydroxy and secondary amine functions. The level of catalyst employed is generally from 1 to 10 parts, preferably 1 to 5 parts, based on 100 parts of azlactone. The azlactone functions of the present invention advantageously prefer attachment to carbohydrated, polypeptide and/or polynucleotide sequences at a terminal end.

The step of attaching biomolecules to the polymer may be carried out before or after coating, before or after curing, and before or after patterning. After biomolecules are attached, capping groups may be added to occupy any unused azlactone functions and prevent later contamination of the gel by any unwanted material. Capping groups preferably react readily with the azlactone and preferably do not interfere with the desired characteristics of the gel. Preferably, the capping group is water soluble and thus improves the swellability of the gel.

The resulting cured gel is advantageously swellable, since a swellable gel may bind a greater amount of the biomolecule in a given area of a substrate. This increase in areal density improves the ability to take measurements such as optical readings of the target site and allows for greater miniaturization. This invention is useful in analytical devices employing biomolecules as test probes or reference standards, in particular where it is desirable to employ a variety of differing biomolecules in a compact area of a substrate. For example, miniaturization of DNA sequencing operations onto microchips offers advantages in speed and cost. Oligonucleotide containing gel pads of the present invention can be used to make high density DNA chips having anywhere from thousands to millions of microelectrodes spotted on the surface of a chip. In the method of sequencing by hybridization, a complete array of oligonucleotide probes (e.g., all 1024 possible pentamers or all 65,536 possible octamers) is patterned onto a substrate and the DNA sample to be sequenced is allowed to specifically hybridize to the array. The hybridization process can take several hours if governed by simple diffusion of the DNA molecules. By applying current or voltage signals to the microlocations of the present invention, DNA samples can be quickly attracted to the individual gel pads for hybridization. Reversing the signal drives off non-specifically bound sample. Repeating the process several times can enhance sample uptake at the correctly specified microlocations on the APEX array. In this application, electrodes can be individually addressed or can be addressed in parallel. In the later case, the electrodes can optionally be connected to a common ground plane. The target DNA sequence can be identified by analysis of the overlapping sets of oligomers that form perfect duplexes with the target sequence. As an example, chips such as these may be useful in applications that require sequencing of multiple gene mutations, as might be required in detecting a polygenic disease.

Low density DNA chips generally can have up to 300 probes and are particularly suited to diagnostic applications where detection of a specific organism or strain or a panel of tests is required. A sample of DNA can be electrophoretically moved from one microlocation to the next. Electronic stringency control can be used to retain the DNA that matches the capture probe at each microlocation.

Microarrays of enzyme-containing gel pads of the present invention can be used to screen chemical compounds for enzyme inhibiting or activating effect. Biomolecules on the surface of microorganisms serve as anchor points for attachment to the gel. The biological response of the microorganisms to chemical stimuli or other environmental conditions can be monitored. Gels containing biological molecules that promote cell attachment and growth (e.g., growth factors or collagen) can be patterned using the methods and compositions describe above. The resultant patterned gels can be used to generate two-dimensional cellular structures.

Also, the individual gel pads may be used as microreactors. For example, polymerase enzyme may be covalently anchored to individual microelectrodes and used to support DNA amplification at specified microlocations. In this case, the electrodes are charged to introduce reagents and transfer amplified products to specified microlocations for further processing.

Devices of the present invention can also be used to support immunoassay panels, panels for drugs of abuse, enzyme based electrodes and optodes. Also, an array of gel pads can be used to soak up a metered amount of fluid containing microorganisms to be detected. Growth nutrients and fluorescent probes can be incorporated in the gel pads. The number of viable organisms in the sample can be related to the number of gel pads that exhibit a fluorescent response.

In addition, devices of the present invention can be used to screen libraries of carbohydrate oligomers for specific affinities to biomolecules such as drug receptors. Carbohydrate oligomers terminated with an amino- or thio-linkage can be covalently attached to azlactone-functional microlocations on the APEX array. A sample containing a specific receptor can be electrophoretically concentrated onto one or more microlocations during the assay. Electronic stringency control can be used to determine relative affinities for the receptor to individual carbohydrate oligomers in the assay.

Flexible APEX arrays of the present invention can be laminated to a structured fluid handling architecture (glass or plastic) designed to direct or confine a fluid to the region above the array of micro-locations on the first surface of the substrate. In a preferred embodiment, a microreplicated plastic film may be laminated to the first surface of a flexible APEX array film such that the resulting laminate may define a series of APEX chips which can be diced into individual devices or stored as a roll good for future use. In this preferred embodiment, the electrode traces and contact pads can be patterned on the second surface of the APEX film, such that the contact pads terminate at the edge of each individual chip, once diced. The microreplicated film preferably can be embossed with features that, when laminated, define a closed sample well above the array of APEX microlocations. Typical dimensions for such a well may be 1 cm×1 cm by 50 µm deep. At least two microreplicated channels may connect this well to sample inlet and outlet ports defined by vias in the microreplicated film. The film may define additional microfluidic processing architectures, as needed.

In use, this chip can be inserted into an APEX controller designed to mate to the inlet and outlet ports as well as the contact pads. The controller can inject a sample onto the chip and optically interrogate the APEX array while actively processing the sample through application of controlled voltages or controlled currents to the individual microelectrodes.

In another embodiment, as shown in FIGS. 10a and 10b, APEX biocard 100 can be prepared by laminating a sheet of APEX film 190, having between 2 and 200 separate APEX arrays 110, shown in FIG. 10A, to a rigid glass or preferably a micromolded plastic fluid-handling architecture 120, in registration with the APEX arrays, to form biocard 100, shown in FIG. 10b. In this embodiment, fluid handling architecture 120 can be designed to define between 2 and 200 independent samples wells 130, one for each APEX array 110, with corresponding inlet channels 140 and outlet channels 150. In this format, between 2 and 200 different biological samples, corresponding to the number of APEX arrays 110 on biocard 100, can each be evaluated. The fluid handling architecture can be simple barriers between APEX arrays (e.g., open wells into which sample is injected, such that the cassette must be horizontal), to closed structures into which sample can be injected with a syringe or pump, such that the cassette can be held in a vertical position.

A machine may also be provided for accepting and operating an APEX biocard or cassette. The APEX biocard controller can comprise a sample injection unit to provide 2 to 200 independent biological samples onto the biocard via ports in the fluid handling architecture. A voltage control unit can simultaneously provide controlled currents or voltages to each of the 2 to 200 APEX arrays in parallel, for electrophoretic processing. A detection system can provide optical, electrical, or mechanical signals in response to biological events at the individual electrodes of each APEX array.

In one embodiment, the intake ports may be configured to receive fluid injection tips and related assembly, through which samples arrive at the APEX arrays, under a vacuum applied to the biocard, which is then released to atmospheric pressure. The injection port optionally may include a small intake reservoir, which acts as a fluid buffer. The fluid (e.g., patient sample or other solution) can enter the intake port, collect in the intake reservoir, and travel along a distribution channel to the sample well. Each fill channel can descend to and enter the sample well at an angle which results in a natural flow of the sample fluid down through the fill channel by gravity. Each of the sample wells may have an associated bubble trap, connected to the sample well and located at a height slightly above the well on the card surface. Each bubble trap can be connected to its respective well by a short conduit.

In operation, each of 2 to 200 samples can be processed simultaneously with one controller unit that operates the bio-card. A single controlled voltage or current source can apply control signals to all of the APEX arrays in parallel. An imaging system mounted on an X-Y stage, moving from one array to the next, can collect optical information about the electrophoretically processed sample on each array.

In yet another embodiment, as shown in FIG. 11, a spool containing roll 210 of APEX film to which a flexible plastic fluid handling architecture has been laminated as described above, is prepared. The fluid handling architecture can be designed to direct 2–10,000 independent biological samples to the corresponding number of independently addressable APEX arrays on APEX film 220 for further processing. Film 220 can be advanced through assay machine 230 that addresses a preselected subset of APEX arrays. Once the samples have been assayed, the spool can be further advanced.

Assay machine 230 may include a sample injection unit to provide biological samples onto the cassette via ports in the fluid handling architecture. A voltage control unit may simultaneously provide processing currents or voltages to each of the APEX arrays that may be resident in assay machine 230. A detection system can provide optical, electrical, or mechanical signals in response to biological events at the individual electrodes of each APEX array.

The invention is further described by the following example:

EXAMPLE

Free Field Electrophoresis on a Microcircuit

A laminated microinterconnect (LMI) circuit essentially identical to that shown in FIG. 1 was prepared according to the method disclosed in U.S. Pat. No. 5,401,913 (Columns 3, 4, and 5, and FIGS. 1–7), comprising a polyimide substrate having copper microcircuit traces on one side. Vias of approximately 60 µm diameter were chemically milled from the side opposite the microcircuits in registration with the copper circuit termini, on a 200 µm pitch.

An aqueous solution containing bovine serum albumin (BSA, Sigma Chemical Co., St. Louis, Mo.) that was labeled with fluorescein isothiocyanate (FITC) in a pH 7.0 phosphate buffered saline buffer (PBS) was applied to the LMI on the side having vias. Electrical connection was made to individual electrodes using platinum microprobes and voltages were applied using a computer-controlled voltage supply. At pH 7.0, the BSA was positively charged and accumulated at negatively biased electrodes. Using a Leica epifluorescence microscope equipped with an L3 filter cube (Leica Microsystems, Inc., Deerfield, Ill.), fluorescence of labeled BSA could be detected at vias where it had accumulated according to the negative bias of the electrodes. Fluorescence was induced by irradiation at 470 nm using a blue LED and monitored at 510 nm by the Leica microscope.

Thus, FITC-labeled BSA was electrophoretically concentrated onto one of the electrodes by applying a 10 Volt bias to that electrode while all other electrodes were grounded. A second electrode within the microscope field of view was then biased at—10 Volts while the first electrode was grounded. Within a few seconds, the labeled BSA was seen to migrate to the second negative electrode. Repeated cycling of charge was accompanied by repeated migration of the labeled BSA.

The above specification and example are believed to provide a complete description of the manufacture and use of particular embodiments of the invention. Many embodiments of the invention can be made without departing from the spirit and scope of the invention.

We claim:

1. An electronic device adapted for performing electrophoresis assisted processes, the device comprising:
    at least one flexible polymeric substrate having a first surface and a second surface; the first surface being opposite the second surface;
    one or more microlocations interrupting the first surface, each of said microlocations including an electrode disposed on the second surface of the flexible substrate and extending to the microlocation; the electrode defining the microlocation or forming a bottom of the microlocation; and
    a hydrophilic matrix positioned on the microlocation and in electrical contact with at least one of the electrodes.

2. The electronic device according to claim 1, wherein the hydrophilic matrix comprises a biologically receptive gel.

3. The electronic device according to claim 1, wherein the hydrophilic matrix comprises a biologically reactive gel.

4. The electronic device according to claim 1, wherein the electrophoresis assisted processes include biological processes.

5. The electronic device according to claim 1, wherein the electrophoresis assisted processes include molecular biological processes.

6. The electronic device according to claim 1, wherein the flexible polymeric substrate comprises polyimide.

7. The electronic device according to claim 1, wherein the plurality of microlocations interrupting the first surface comprise vias that extend from the first surface into the polymeric substrate.

8. The electronic device according to claim 1, wherein the plurality of microlocations interrupting the first surface further comprise a raised area of electrically conductive material.

9. The electronic device according to claim 1, wherein the microlocations have a smallest dimension in the plane of the first surface of less than 200 µm.

10. The electronic device of claim 1, wherein the hydrophilic matrix composes an azlactone functional polymer.

11. The electronic device according to claim 1, wherein a portion of the first surface, the second surface, or both surfaces is partially masked.

12. The electronic device according to claim 1, further comprising a plurality of conductive traces, each trace connected to at least one of said electrodes.

13. The electronic device according to claim 1 additionally comprising at least one electroresistive layer positioned adjacent to at least one electrode.

14. The electronic device according to claim 13 wherein at least one electroresistive layer can function to increase the temperature of at least one electrode.

15. An electronic device adapted for performing electrophoresis assisted processes, the device comprising:
    at least a first flexible polymeric substrate having a first surface and a second surface; the first surface being opposite the second surface;
    at least a second flexible polymeric substrate, having a first surface adjacent the second surface of the first polymeric substrate;
    at least one microlocation penetrating the first polymeric substrate and the second polymeric substrate in registration, each of the microlocations including an electrode disposed on the second surface of the second polymeric substrate; the electrode forming a bottom of the microlocation; and
    a hydrophilic matrix positioned on the microlocation and in electrical contact with at least one of the electrodes on the second surface of the second polymeric substrate.

16. An electronic device adapted for performing electrophoresis assisted processes, the device comprising:
    at least one flexible polymeric substrate having a first major surface;
    one or more microlocations disposed on the first major surface of the substrate, each of the microlocations including an electrode; the electrode defining the microlocation or forming a bottom of the microlocation; and
    a hydrophilic matrix positioned on the microlocation and in electrical contact with at least one of the electrodes disposed thereon.

17. The electronic device according to claim 16, further comprising a fluid, handling architecture sealingly engaged with said first surface in registration with said microlocations.

18. The electronic device according to claim 17 wherein said fluid handling architecture comprises a micromolded plastic fluid handling architecture.

19. A flexible polymeric sheet containing a plurality of addressable programmable electronic matrix (APEX) arrays, wherein the plurality of arrays are configured on a substantially continuous sheet, each array adapted for performing an electrophoresis-assisted process, each of the arrays comprising:
    a flexible polymeric substrate having a first surface and a second surface; the first surface being opposite the second surface;
    a hydrophilic matrix including an azlactone-functional polymer positioned on the first surface of the flexible polymeric substrate; and
    a plurality of microlocations interrupting the first surface, each of said microlocations including an electrode disposed on the second surface of the flexible substrate and extending to the microlocation; the electrode defining the microlocation or forming a bottom of the microlocation.

20. The flexible polymeric sheet according to claim 19, wherein the flexible polymeric substrate comprises polyimide.

21. The flexible polymeric sheet according to claim 19, further comprising:
   a second surface on the flexible polymeric substrate; and
   an electrode disposed on the second surface;
   wherein an electrode is located adjacent to each of said microlocations and the hydrophilic matrix is in electrical contact with the electrode.

22. The flexible polymeric sheet according to claim 21 comprising from 1 to 200 APEX arrays.

23. A biocard comprising a flexible polymeric sheet according to claim 22 mated in registration on the first surface with a fluid handling architecture.

24. The biocard according to claim 23, wherein said fluid handling architecture comprises a molded flexible polymeric part.

25. A method of making an electronic device adapted for performing molecular biological processes, the method comprising:
   providing a flexible polymeric substrate having a first surface and a second surface; the first surface being opposite the second surface; wherein the flexible polymeric substrate is substantially continuous;
   forming a plurality of microlocation interrupting the first surface, each of said microlocations including an electrode disposed on the second surface of the flexible substrate and extending to the microlocation; the electrode defining the microlocation or forming a bottom of the microlocation; and
   applying a hydrophilic matrix including an azlactone-functional polymer on at least one of the first surface of the flexible substrate and the microlocations, wherein the hydrophilic matrix makes electrical contact with the electrode.

26. The method according to claim 25, further comprising the step of applying at least one of a biological material and a chemical material to at least one of the microlocations.

27. A method of performing molecular biological processes, the method comprising:
   providing an electronic device comprising:
      a flexible polymeric substrate having a first and second surface; the first surface being opposite the second surface; wherein the flexible polymeric substrate is substantially continuous;
      one or more microlocations interrupting the first surface, each of said microlocations including an electrode disposed on the second surface of the flexible substrate and extending to the microlocation; the electrode defining the microlocation or forming a bottom of the microlocation, and
      a hydrophilic matrix including an azlactone-functional polymer positioned on the first surface of the flexible substrate and an electrode disposed on the second surface of the flexible substrate, the hydrophilic matrix positioned such that it is in electrical contact with the electrode;
   placing a biological sample on the hydrophilic matrix; and
   applying an electrical force to the electrode so as to effect a transfer or transformation of the biological sample.

28. The method according to claim 27 further comprising performing from 1 to 200 molecular biological processes, wherein the processes are carried out according to at least one of simultaneous processes and serial processes.

* * * * *

UNITED STATES PATENT AND TRADEMARK OFFICE
CERTIFICATE OF CORRECTION

PATENT NO.        : 7,220,344 B2
APPLICATION NO. : 10/200829
DATED             : May 22, 2007
INVENTOR(S)       : James G. Bentsen It is certified that error appears in the above-identified patent and that said Letters Patent is hereby corrected as shown below:

<u>Column 7</u>
Line 21, delete "DESCRIPTIONS" and insert in place thereof -- DESCRIPTION --.

<u>Column 11</u>
Line 42 (approx.), delete "aziactone" and insert in place thereof -- azlactone --.

Line 52, delete "(".

<u>Column 13</u>
Lines 38-43, delete "Suitable...diamines." and insert the same on line 37, after "functions" as a continuing paragraph.

<u>Column 17</u>
Line 42, delete "10$a$ and 10$b$" and insert in place thereof -- 10A and 10B --.

Line 48, delete "10$b$" and insert in place thereof -- 10B"--.

<u>Column 19</u>
Line 63, in Claim 10, delete "of" and insert in place thereof -- according to --.

Line 64, in Claim 10, delete "composes" and insert in place thereof -- comprises --.

<u>Column 20</u>
Line 41, in Claim 17. delete "fluid," and insert in place thereof -- fluid --.

UNITED STATES PATENT AND TRADEMARK OFFICE
CERTIFICATE OF CORRECTION

PATENT NO. : 7,220,344 B2
APPLICATION NO. : 10/200829
DATED : May 22, 2007
INVENTOR(S) : James G. Bentsen It is certified that error appears in the above-identified patent and that said Letters Patent is hereby corrected as shown below:

<u>Column 21</u>
Line 23 in Claim 25, delete "microlocation" and insert in place thereof
-- microlocations --.

Signed and Sealed this

Seventh Day of August, 2007

JON W. DUDAS
*Director of the United States Patent and Trademark Office*